United States Patent
Glazer et al.

(10) Patent No.: US 6,428,667 B1
(45) Date of Patent: *Aug. 6, 2002

(54) MULTICHROMOPHORE FLUORESCENT PROBES USING DNA INTERCALATION COMPLEXES

(75) Inventors: Alexander N. Glazer, Orinda; Richard A. Mathies, El Cerrito, both of CA (US); Konan Peck, Taipei (TW)

(73) Assignee: The Regents of the University of California, Berkeley, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/686,147

(22) Filed: Oct. 10, 2000

Related U.S. Application Data

(60) Division of application No. 08/966,398, filed on Nov. 7, 1997, now Pat. No. 6,280,933, which is a continuation of application No. 08/161,231, filed on Dec. 2, 1993, now Pat. No. 5,763,162, which is a continuation of application No. 07/831,823, filed on Feb. 6, 1992, now abandoned, which is a continuation-in-part of application No. 07/493,307, filed on Mar. 14, 1990, now abandoned.

(51) Int. Cl.[7] .......................... B01D 57/02; C12Q 1/68; C12P 19/34; G01N 33/00
(52) U.S. Cl. .................... 204/456; 435/6; 435/91.1; 436/94
(58) Field of Search .................... 435/6, 91.1, 183; 436/94; 336/23.1, 24.3, 24.33, 25.32; 204/450, 456

(56) References Cited

U.S. PATENT DOCUMENTS

| | | |
|---|---|---|
| 4,119,521 A | 10/1978 | Chirikjian |
| 4,737,454 A | 4/1988 | Dattagupta et al. |
| 4,748,111 A | 5/1988 | Dattagupta et al. |
| 4,743,535 A | 6/1988 | Carrico et al. |
| 5,312,921 A | 5/1994 | Glazer et al. |
| 5,401,847 A | 3/1995 | Glazer et al. |
| 5,763,162 A | * 6/1998 | Glazer et al. .......... 435/6 |
| 5,767,267 A | 6/1998 | Glazer et al. |
| 5,977,344 A | 11/1999 | Glazer et al. |

OTHER PUBLICATIONS

Kroczek, "Immediate Visualization of Blotted RNA" *Nucleic Acid Res.* (1989), vol. 17:9497.
Gangain, et al. "DNA Fuctional Intercalators" *biochemistry*(1978) vol. 17 (24):5078–5088.
Southern, "Detection of Specific Sequences", J.*Mol. Biol.* (1975) vol. 98:503–517.
Sharp et al., "Dection of two Restriction", *Biochemistry*(1973) vol. 12 (16):3055–3063.
Markovitz et al., "Dynamic Structure of DNA Complexes ..."*Biochemistry*(1893) vol. 22:3231–3237.
Gaugain et al. "DNA Bifunctional Intercalators ...", *Biochemistry*(1978) vol. 17:5071–5077.
Markovit et al. Effect of B–Z Transition ..., *nucleic Acids res.* (1985) 13: 3773–3788.
Sayavedra–Soto, "Rapid Visualization of Genomic DNA ..."*Biotechniques*(1990) 8:36–37.
Rosen et al., "An Alternative ..." *Focus* (1990) 12:23–24.
Nielsen et al., *Biochemistry* (1988) 27:67–73.
Markovitz et al., *Anal. Biochemistry* (1979) 94:259–264.
Maniatis et al., "Molecular Cloning" (2[nd]ed. 1989) p. 6–13.

* cited by examiner

*Primary Examiner*—Ethan C. Whisenant
*Assistant Examiner*—Frank Lu
(74) *Attorney, Agent, or Firm*—Bret E. Field; Bozicevic, Field & Francis

(57) ABSTRACT

Novel fluorescent labeling techniques and fluorescent labels are provided, employing high affinity non-covalently binding and intercalating fluorescent dyes and dsDNA. The dyes find application to provide highly sensitive labeling of nucleic acids in electrophoretic gels and as pre-prepared labels for binding to a wide variety of specific binding pair members. The DNA-dye fluorescer complex can be used for labels in diagnostic assays, detection of specific nucleic acid sequences, and the like.

10 Claims, No Drawings

MULTICHROMOPHORE FLUORESCENT PROBES USING DNA INTERCALATION COMPLEXES

CROSS-REFERENCE TO RELATED APPLICATION

This application is a divisional of application Ser. No. 08/966,398 filed Nov. 7, 1997 and now issued as U.S. Pat. No. 6,280,933; which application is a continuation of application Ser. No. 08/161,231 filed Dec. 2, 1993 and now issued as U.S. Pat. No. 5,763,162; which application is a continuation of application Ser. No. 07/831,823, filed on Feb. 6, 1992, now abandoned; which application is a continuation-in-part of application Ser. No. 07/493,307 filed on Mar. 14, 1990, now abandoned; the disclosures of which are herein incorporated by reference.

INTRODUCTION

1. Technical Field

The field of this invention is fluorescent compositions and methods employing fluorescent compositions.

2. Background

Detection of fluorescent signals finds wide applications in a variety of situations and under a variety of conditions. Fluorescence has many advantages as a means of generating a detectable signal. Fluorescence does not suffer from the many disadvantages of a radioactive label, while in many cases it provides for a high level of sensitivity. Instrumentation for detection of fluorescence is readily available and fluorescent labels have found application in such diverse situations as immunodiagnostics, detection of nucleic acid bands in gel electrophoresis and in fluorescence activated cell sorters. The sensitivity of the fluorescent signal depends upon a number of factors: the possibility of self quenching, the effect of other molecules associated with the fluorescent molecule on the quantum efficiency of the fluorescence, the effect of the medium on the quantum efficiency and fluorescence characteristics of the fluorescer; the stability of the fluorescer to light, the ability to remove background fluorescence, and the like.

Desirably, we would wish to have a fluorescent label which was stable, both chemically and to light, provided a high quantum efficiency, was relatively insensitive to interactions with a variety of molecules, as well as variations in medium, had high light absorption and emission characteristics, was relatively insensitive to self-quenching, and could be readily attached to a wide variety of molecules under varying conditions without adversely affecting the fluorescent characteristics.

Relevant Literature

The following references describe DNA intercalating fluorescent dimers and their physical characteristics: Gaugain et al., Biochemistry 17, 5071–5078, 1978; Gaugain et al., Biochemistry 17, 5078–5088, 1978; Markovits et al., Anal. Biochemistry 94, 259–269, 1979; Markovits Biochemistry 22, 3231–3237, 1983; and Markovits et al., Nucl. Acids Res. 13, 3773–3788, 1985. Interaction of various intercalating compounds with nucleic acids is reviewed by Berman and Young, *Ann. Rev. Biophys. Bioeng.* (1986) 10:87–224. Retention of ethidium bromide on electrophoresis of the dye with DNA or RNA is described by Angemuller and Sayavedra-Soto, Biotechniques 8, 36, 1990 and Rosen and villa-Komaroff, Focus 12, 23, 1990.

SUMMARY OF THE INVENTION

Methods and compositions are provided for detecting molecules using fluorescent labels, where fluorescent intercalating molecules having strong binding affinities for nucleic acids are employed. The nucleic acid acts as a scaffold for the fluorescent non-covalently binding and intercalating compounds, minimizing self-quenching and providing for high fluorescence efficiency. The fluorescent labeling finds use in electrophoresis, diagnostic assays, cell labeling, and the like.

DESCRIPTION OF THE SPECIFIC EMBODIMENTS

Novel methods and compositions are provided employing nucleic acid intercalating moieties, having at least one, usually at least two, fluorescent monomeric units, where the monomeric units have affinity for dsDNA (double stranded DNA). In considering the subject compositions a nucleic acid monointercalator complex intends a complex with one dye molecule, whether the dye molecule has a single or plurality of fluorescent monomeric units. A dye nucleic acid aggregate is an assemblage of nucleic acid containing many non-covalently bound and intercalated dye molecules.

The nucleic acid may be single stranded (ss) usually having hairpins, or double stranded (ds), RNA, DNA or combinations thereof, particularly dsDNA.

The monomers will have high binding affinity to the nucleic acid, generally having two or more positive charges. The multimeric compounds will also have high binding affinity for nucleic acids, although fewer than all the fluorescent intercalating units may non-covalently bind and intercalate, e.g., only one unit of a dimer, where each unit will have at least one positive charge, usually at least about two positive charges per unit.

The intercalating compounds may be monomers or homo- or heteropolymers with an affinity for dsDNA of at least about $5 \times 10^6$ $M^{-1}$, more usually at least about $10^7$ and greater than about $10^9$ $M^{-1}$ at ionic strengths of at least about 0.01 usually at least about 0.04, preferably at least about 0.2 at 25° C. Gel electrophoresis is usually performed at an ionic strength of about 0.04.

The compounds are further characterized by employing fluorescent monomeric units which are cyclic, polycyclic, particularly polycyclic aromatic having at least two rings, usually at least three rings, and not more than about six rings, more usually not more than five rings, where at least two of the rings are fused, usually at least three of the rings. The aromatic compound may be carbocyclic or heterocyclic, particularly having from one to three, more usually one to two nitrogen atoms, as annular atoms. The monomeric units will be joined by a linking chain which will normally be of a length to allow for simultaneous intercalation to adjacent monomeric units in dsDNA, usually providing a length of at least about ten Angstroms, usually having at least about 9 atoms, more usually at least about ten atoms in the chain, and usually not more than about 26, more usually not more than 20 atoms, between fluorescent units. The linking group will usually be aliphatic, having from 0 to 8, more usually from 0 to 6, preferably from about 2 to 6 heteroatoms in the chain, particularly heteroatoms which provide for a positive charge, e.g. nitrogen and sulfur. Preferably, there will be at least one positive charge, more preferably at least two positive charges, usually not more than about 8 positive charges, more usually not more than about 6 positive charges.

The rings may be substituted by a wide variety of substituents, which substituents may include alkyl groups of from 1 to 4 carbon atoms, usually from 1 to 2 carbon atoms, oxy, which includes hydroxy, alkoxy and carboxy, generally of from 1 to 4 carbon atoms, amino, including mono- and disubstituted amino, particularly mono- and dialkylamino, thio, particularly alkylthio of from 1 to 4, usually 1 to 2 carbon atoms, cyano, nonoxo-carbonyl, such as carboxy, particular carboxamide or carboalkoxy, of from 2 to 6, usually 2 to 4 carbon atoms, oxo-carbonyl or acyl, generally of from 1 to 4 carbon atoms, halo, particularly of atomic number 9 to 35, etc.

The polymers will have at least two monomeric units and usually not more than 12 monomeric units, more usually not more than about 8 monomeric units, preferably not more than about 4 monomeric units.

Polycyclic compounds which find use include phenanthridines, acridines, porphyrins, phenylindoles, and bisbenzimides. Derivatives of these compounds which find use include, bis-(3,8-diamino-6-hydroxy-6-phenyl-5,6-dihydrophenanthridine, di-(7-hydropyridocarbazoles), tetraacridinylamine, hexa-acridinylamine, thiazole orange dimer, 5-(11-(2-methoxy-6-chloro-9-aminoacridinyl)-( 4,8-diazaundecyl)-3,8-diamino-6-phenylphenan-thridinium chloride, and the like.

Compounds can be prepared from alkylene polyamines, where the alkylene groups are of from 2–10, usually 2–6 carbon atoms, and haloalkyl- or pseudohaloalkyl substituted fluorescent polycyclic aromatic compounds, e.g., phenanthridines or acridines, which may be substituted or unsubstituted, to provide for ternary or quaternary amino groups. The amino groups may be quaternized with any convenient alkylation agent, either before or after reaction with the fluorescent compound or may be prepared initially as ternary amines using alkylamines, where the alkyl group will be of from about 1–6, usually 1–3 carbon atoms. Illustrative of a compound would be N, N, N', N'', N'',-pentamethyl-N, N', N''-tris-(3,8-diamino-6-hydroxy-6-phenyl-5,6-dihydrophenanthridine).

These compounds find use as labeling agents, where the compounds are used in a process for detection of nucleic acid or as a label which is prepared for labeling a compound to provide a fluorescent signal.

The first situation is exemplified by separations employing an electrical field, e.g. electrophoresis. In employing the subject compounds, the nucleic acid, usually, DNA, and the dye may be brought together in an appropriately buffered medium and incubated for sufficient time for the dye to non-covalently bind and intercalate in the nucleic acid. The dye employed will usually be a multimer, usually at least a dimer. The ratio of dye to ds nucleic acid may be varied widely ranging from about one molecule of dye per base pair, to as little as one molecule of dye per twenty base pairs, depending upon the desired degree of sensitivity. Dye present in excess of one dye per four base pairs, or more, does not significantly influence the results, so that any increase in the amount of dye above a mole ratio of one dye molecule per four base pairs will normally be undesirable. Generally, the amount of dye will range from about one molecule per 4 to 5 base pairs for optimum results.

The amount of nucleic acid will generally be conventional amounts employed for electrophoresis, generally ranging from about 0.005 ng/$\mu$l to 5 ng/$\mu$l. Various conventional buffers may be employed, such as tris-acetate or tris-borate, generally present in the range of about 1 to 50 mM, more usually in the range of about 1–20 mM, to provide a pH in the range of about 5 to 10, more usually about 7 to 9. Also, a metal ion chelator may be present in minor amount, generally from about 0.05 to 0.5 mM. Conveniently, EDTA may be employed.

The dye and nucleic acid may be incubated, usually for at least 5 minutes and not more than about 2 hours, where complex formation will normally be complete in less than about one hour, usually in about 30 min. at room temperature. The incubated solution may be used directly or further diluted, as appropriate, prior to application to the gel.

Tracking dyes may or may not be used, since it is found that the tracking dyes tend to interfere with the detection of the non-covalently bound and intercalated dye. Also, gels may be subjected to pre-electrophoresis for sufficient time to decrease background fluorescence, usually not more than about six hours, preferably not more than about three hours.

The electrophoresis may be performed in any convenient and conventional manner, where the bands may now be detected by fluorescence of the non-covalently bound and intercalated dye. The electrophoresis insures that unbound dye is removed from the region of the bands and the dye is found to be retained in the nucleic acid, so that individual bands may readily be detected by fluorescence scanning.

Any conventional detection system may be employed for detecting the individual bands, conveniently the same detection systems employed for the detection of ethidium bromide. Depending on the particular dye employed, the excitation light will be chosen to be within a major absorption band of the dye.

Of particular interest is the use of a confocal laser scanning fluorescence imaging system. For ethidium dimer, the fluorescence can be excited with a laser. A system which has been found to be convenient employs a long pass dichroic beam splitter to reflect the laser beam down through a microscope objective and onto the sample. The fluorescence emission is collected by the objective and passed through the beam splitter to a photodetector. The fluorescence emission is then passed through a spatial filter to effect confocal detection and a long pass or bandpass color or interference filter before reaching a photomultiplier tube. An appropriate servo motor-driven XY translation stage is employed with a 2.5 $\mu$m resolution to translate the gel past the laser beam at a convenient speed, generally about 1–5 cm/sec. A microcomputer may be employed to control the XY translation stage and to acquire and display images. The fluorescence images may then be pseudo-color encoded to represent different intensity levels and contrast stretched with a histogram equalization method to enhance the images. To quantitate the image data, the image columns that enclose the nucleic acid bands may be extracted and integrated.

The nucleic acid may be readily isolated free of the intercalated fluorescent dye for further use. One may use the Geneclean® kit for recovery of 50% or better of the nucleic acid. By combining the intercalated dye containing nucleic acid with Glassmilk in an aqueous solution of alkali metal iodide, e.g. 1–10 ng nucleic acid (1–5 $\mu$g/ml nucleic acid) and about 1–10 $\mu$g/ml of Glassmilk, incubating with agitation for about 5–60 mins. followed by centrifugation, the resulting pellet is isolated. After resuspending the pellet in an appropriate ethanolic buffered aqueous solution (e.g. 1:1] followed by centrifugation and repeating this washing procedure, the nuclei acid is obtained substantially free of the fluorescent dye.

By virtue of the use of the subject intercalating fluorescent dyes in the electrophoresis, greatly enhanced sensitivities are achieved due to the much higher level of fluorescence intensity which is obtained. Sizes and amounts of DNA fragments in mixtures of unknown composition can be determined with a total amount of material ranging from 100 pg to 1 ng depending on the complexity of the mixture and the size range o the fragments. Thus, the subject method can find application in the detection of nucleic acid of less than about 5 ng, particularly less than about 1 ng, frequently less than about 100 pg, even less than about 50 pg.

Instead of employing the subject dyes for detection of nucleic acid bands in electrophoresis, compositions comprising dsDNA and the subject dyes at substantial saturation may be employed, where the dsDNA is joined to an entity for binding to another entity, either covalently or non-covalently. The entities will be either referred to as specific binding pairs, since the entities will have specific affinity for a complementary entity, as compared to diverse other types of molecules, or covalently binding functionalities for reacting with other molecules, such as polypeptides or saccharides.

The specific binding pairs may involve a wide variety of molecules, which are arbitrarily called ligands and receptors. For the subject invention, the ligands and receptors may include a wide variety of proteins, such as antibodies, specific binding proteins, such as surface membrane protein receptors, lectins, blood proteins, and the like, carbohydrates, small organic molecules, both naturally occurring and synthetic to which proteins specifically bind, either naturally occurring protein receptors or antibodies, nucleic acids which may hybridize or specifically bind to an homologous or partially homologous sequence usually having at least about 30% complementarity, preferably at least about 50% complementarity over the complementary region, and the like. In effect, any two molecules which have a specific binding affinity may be employed, so that the label may be used for detection of the presence of the complementary member. The desired specificity may be varied widely, depending upon the particular nature of the molecules to be detected, the information desired about the nature of the sample, or the like.

The labels may be used for detecting any of a wide variety of molecules in a wide variety of samples, which includes physiological samples, e.g. blood, plasma, urine, spinal fluid, saliva, feces, mucus, etc., waste samples, from processing, garbage, soil, water, etc., contaminants in products, such as food, drugs, etc.

Depending upon the fluorescence intensity one desires, one can vary the length of the dsDNA and the level of non-covalent binding and intercalation to increase the fluorescence intensity per molecule. Usually, there will be at least about 16 base pairs, more usually at least 20 base pairs, and one may have the dsDNA of at least about 1 kbp or even 2 kbp or more. The particular length of the dsDNA is not critical to this invention and may be varied in accordance with the fluorescence intensity desired per molecule, purpose of the label, convenience, and the like. It is found that with some dyes, e.g. ethidium-acridine heterodimer, there is an increase in fluorescence intensity by having A-T pairs. Thus, one may provide for a poly A-T.poly A-T dimer to be used as the label. However, if one wishes to further increase the stability of the dsDNA, beyond that which the intercalating dimer provides, one can use a combination of AT and CC pairs or a poly G-C.poly G-C dsDNA. Alternatively, one may use any source of random DNA, such as calf thymus DNA, *E. coli* DNA, etc.

The dsDNA should provide for means for binding to another molecule. This can be achieved in a wide variety of ways, depending upon the manner in which the label is to be employed. For example, the dsDNA may include biotin conjugated nucleotides, one or more biotins, where the biotin will bind to avidin or streptavidin (hereafter both will be referred to as "avidin"). The biotins may vary from one biotin per nucleotide to 0.1% of the nucleotides depending on the nature of the procedures, conditions, etc. Alteratively, any molecule may be employed, particularly a small organic molecule (less than about 2 kdal) which is unlikely to be encountered in the sample of interest, where the small organic molecule has a specific receptor or antibody, particularly monoclonal antibody, to which it specifically binds. Thus, thyroxine, corticosteroids, estrogens, retinoic acid, mannose and the like may be used with proteins which bind specifically to such molecules. Alternatively, synthetic molecules may be employed for which antibodies have been produced, such as 2,4-dinitrophenyl, barbiturate, phosphatidylcholine, etc. These molecules may be included during synthesis of the DNA by being linked to an internal or terminal nucleotide, where the DNA is synthesized in accordance with conventional automatic procedures, or may be added after synthesis of the DNA by linking to either available hydroxyl or amino groups.

The binding entity may be an active functionality for covalently bonding to a molecule having a functionality capable of forming a stable covalent link, such as amino, hydroxyl, thio, carboxyl, activated olefin or aryl, or the like where the functionality to other than a naturally occurring functionality of the nucleotide. The label may be modified with an activated olefin, such as maleyl, for reaction with a thiol group, a carboxyl for reaction with an amine, or the like. In this manner, many different types of molecules may be fluorescent labeled for use in diagnostics, both competitive assays and non-competitive assays, histology, cytology, separations e.g. electrophoresis, HPLC, FACS, and the like.

The strands of DNA may take various structures. In many situations, the dsDNA may comprise two strands, where the strands may be completely or only partially overlapping, where the ends may extend in the 5' and/or 3' directions, so that one strand may be substantially longer than the other strand, where the other strand may bind either 5' proximal, 3' proximal or centrally. Alternatively, the two strands may overlap to provide for staggered ends, where the single stranded portions of the DNA may then be used to bind to complementary sequences. Alternatively, one may provide a single strand with an inverted repeat, so that the strand loops back on itself to provide the double stranded portion. The hairpin structure may be used solely for labeling, or a single stranded portion of the hairpin may be employed for hybridizing to a complementary sequence. The hybridizing single stranded portion may be an extension at either the 5' or 3' end to provide for a staggered terminus or may be present in the loop of the hairpin.

The subject labels may be used in a wide variety of environments and contexts to provide for high levels of fluorescence intensity without interference from the molecules to which the labels bind, either directly or indirectly, the media employed, the conditions employed, and the like. Thus, the subject labels may be employed in specific binding pair assays, where the label may be readily linked to another molecule through a specific binding pair combination. For example, in diagnostic assays, one may combine an avidin conjugated antibody, where the antibody binds to a molecule of interest, to biotin labeled DNA dye aggregate to provide for fluorescent labeled antibody.

Alternatively, the antibody may be labeled with biotin, so that avidin may act as a bridge between the biotin labeled antibody and the biotin labeled DNA dye aggregate. In this way, the fluorescent label may be added after combining the sample with a complementary specific binding pair member and carrying out the assay, followed by addition of label and removal of any nonspecifically bound label.

Where a single stranded DNA sequence is provided as part of the label, this can be used for hybridizing to complementary DNA or RNA sequences. The presence of the non-covalently bound and intercalated dye greatly enhances the stability of the dsDNA. Thus, one can introduce the subject labels into a denaturation medium under conditions where the non-covalently bound and intercalated dsDNA will be stable, while the sample DNA may be denatured to provide for single strands. Where single stranded DNA or RNA is present, there will be no need for providing for denaturation conditions. Therefore, the subject molecules may be used as probes to identify DNA sequences under a wide variety of conditions, including electrophoresis, polymerase chain reactions, where the single stranded sequence may serve as a primer, in Southern blotting, Northern blotting and the like.

Instead of having non-covalent complexes between the non-nucleic acid specific binding pair member and the DNA dye aggregate, one can provide for covalent bonding. Thus, by providing for activated groups such as carboxy, diazo, activated ethylene, or the like, the fluorescent moiety may be readily linked to other molecules, such as proteins, sugars, lipids, or the like by employing conventional linking groups resulting in amide, amines, diazo, esters, thioethers, and the like. For example, one may introduce a thiol group at either the 3' or 5' terminus of a synthetic oligonucleotide, synthesize the complementary strand and form a non-covalently bound and intercalated dye complex. The thiol group on the DNA can then be reacted with a maleimide modified protein, e.g. an antibody. Other techniques may follow conventional procedures found in the literature.

The subject DNA dye aggregate may also be used in situations where one wishes to transfer energy or receive energy from another molecule. Thus, the subject compositions may be used with other fluorescent dye substituted molecules, e.g. dye intercalated DNA molecules, for receipt or transfer of excitation energy, or with other fluorescent molecules, so. as to extend the shift between the excitation light and the emission light. This technique may be used in diagnostic assays, or where one wishes to determine the spatial relationship between two entities, e.g. epitopes, surface membrane receptors, etc.

One may also use the subject labels in a fluorescence activated cell sorter to provide for greatly enhanced sensitivity as a result of the substantially increased fluorescence intensity. Again, one may use ligands for surface membrane receptor proteins, sugars for lectins, antibodies for epitopes present on the surface of the cell, or the like, where the subject labels may be bound covalently or non covalently to the molecule which binds to the cell component.

With the subject compositions one can also detect proteins to transcriptional initiation elements, e.g. promoters, operators, enhancers, etc. By having labeled dsDNA, according to the subject invention, mixed with labeled proteins, labeled with a fluorescent molecule emitting at a different wavelength from the non-covalently bound and intercalated fluorescer, or other appropriate label, one can determine the presence of transcription factors and cofactors. For example, one can gel electrophorese the mixture and identify the presence of the protein bound to DNA by virtue of the double labelling.

One may also use the subject fluorescent non-covalently bound and intercalated DNA for in situ hybridization studies, intermolecular transfer of fluorescent molecules from one doubly stranded nucleic acid molecule to another, e.g. for transferring fluorescent dye without the fluorescer being transferred to the medium. This may find use in making chromosomes with triplex formation, in transferring to nucleic acid in a gel or on a membrane, etc. The fluorescer intercalated DNA may be bound to a particle, e.g. magnetic, to be removed after use as transfer agent.

The subject compounds may be used with advantage with a cofocal fluorescence imaging system. With this system less than 100 pg of DNA can be detected and with some dyes, e.g. thiazole orange dimer, less than about 5 pg of DNA can be detected.

In histology and cytology the subject fluorescent labels provide for high sensitivity in detecting target epitopes, particularly at low levels.

The following examples are offered by way of illustration and not by way of limitation.

MATERIALS AND METHODS

DNA Samples. Standard mixtures, λDNA/Hind III fragments and 1 kbp DNA ladder, were obtained from ethesda Research Laboratories. A preparation of pUC18 purified on a CSCl gradient and a polymerase chain reaction mixture were provided by Dr. Jeffrey C. Gingrich (Human Genome Center, Lawrence Berkeley Laboratory, Berkeley, Calif.). The polymerase chain reaction mixture was obtained by using a primer, Alu3 (CCTGTAATCCCAGCACTTTG), with a yeast artificial chromosome containing a −350 kbp insert of human DNA derived from chromosome 21 and amplified for 30 cycles.

Reagents. Ethidium homodimer (EthD; E=8,900 $M^{-1}cm^{-1}$ at 492 nm; lot #9A), obtained from Molecular Probes, Inc., was stored in the dark as a stock solution at 1 mg/ml in 0.04 M Tris-acetate buffer, pH 8.4, at 4° C. Under these storage conditions, less than 4% decomposition of the dye was observed over a period of a month as determined by absorption spectroscopy. Ultrapure agarose was obtained from Bethesda Research Laboratories and Ficoll (type 400) from Sigma. The Geneclean kit was obtained from BIO 101, Inc. All other reagents were of the highest commercially available grade.

Complex formation and agarose gel electrophoresis. Mixtures of DNA (1.5 to 0.05 ng/μl) and EthD (0.3 to 0.015 ng/μl), at varying DNA/dye ratios, were prepared in 4 mM Tris acetate −0.1 mM EDTA, pH 8.2, under subdued illumination and kept in the dark. Fluorescence emission spectroscopy and gel scanning indicated that complex formation was complete within 30 min at room temperature. The mixtures were routinely incubated for 60 min prior to application to the agarose gel unless otherwise indicated. Immediately prior to electrophoresis, one part of 15% (w/v) Ficoll in water was added to 3 parts of sample, by volume. Aliquots (4 μl) of sample were then applied to 5 mm-wide wells in 1 mm thick, 7 cm long, vertical 0.9% (w/v) agarose gels prepared in 0.04 M Tris acetate −1 mM EDTA, pH 8.4. Electrophoresis was performed in the same buffer in a Bio-Rad Mini-Protean II electrophoresis cell at 5 V/cm in the dark. Tracking dyes were not used; the commonly used dyes, xylene cyanole FF and bromophenol blue, are fluorescent and interfere in the detection. Gels were subjected to pre-electrophoresis for 2–3 hours prior to sample application to decrease background fluorescence.

Competition for EthD between preformed λDNA/Hind III complexes and excess pUC18 DNA. All solutions were in 4 mM Tris acetate −0.1 mM EDTA, pH 8.2, at 23° C. (a) A mixture of λDNA/Hind III fragments and EthD (100 ng DNA+12.5 ng EthD in 150 μl of buffer) was incubated for 60 min. pUC18 DNA (5 μg in 5 μl of buffer) was then added and the mixture allowed to stand for a further sixty minutes. Two control mixtures, (b) and (c) were prepared as follows. (b) A mixture of DNA/Hind III fragments and EthD (100 ng DNA+12.5 ng EthD in 150 μl of buffer) was incubated for 60 min. (c) A mixture of pUC18 DNA and EthD (5 μg DNA+12.5 ng EthD in 150 μl of buffer) was incubated for sixty minutes. At the end of the times indicated above, 50 μl of Ficoll (15% w/v in H20) were added to each of the three mixtures and 4 μl of each sample applied to an agarose gel. Additional experiments performed in the manner described above included a control mixture in which the λDNA/Hind III fragments (100 ng) and the pUC18 DNA (5 μg) were mixed before the addition of EthD, and mixtures of pre-formed λDNA/Hind III-EthD complexes with pUC18 DNA prepared as described for (a) above, but incubated for periods of time up to six hours.

Removal of bound EthD by the Geneclean procedure. The procedure described below is based on the brochure provided by the manufacturer with the Geneclean kit. The recovery of λDNA/Hind III fragments was about 50%. λDNA/Hind III fragments (0.4 ml; 4.76 ng DNA/μl) were mixed with EthD (0.4 ml; 1 ng/μg), both in 4 mM Tris acetate-0.1 mM EDTA, pH 8.2, and kept in the dark for 60 min. To 0.4 ml of the above mixture was added 1.0 ml of 6 M NaI and 5 μl of Glassmilk suspension in sterile water. The DNA was allowed to bind for 15 min with periodic agitation. The Glassmilk was then pelleted by a brief spin in a microcentrifuge and the NaI-containing supernatant was discarded. The pellet was resuspended by vortexing in 900 μl -50% (v/v) ethanol in Tris-EDTA buffer and then centrifuged again. This washing procedure was performed three times. The pellet was then resuspended in 40 μl of 4 mM Tris acetate-0.1 mM EDTA, pH 8.2. To one 8 μl aliquot of the eluate was added 142 μl of 4 mM Tris acetate-0.1 mM EDTA, pH 8.2, and to a second 8 μl aliquot was added 142 μl of the same buffer containing 10 ng EthD. These mixtures were kept for an hour in the dark. Fifty μl of Ficoll (15% w/v in H₂O) were added to each sample and a 4 μl aliquot of each sample applied to an agarose gel. A suitably diluted aliquot of the portion of the original λDNA/Hind III-EthD mixture, not exposed to the Geneclean procedure, was also applied to the same gel as an additional control.

Fluorescence detection and quantitation of DNA-EthD complexes on agarose gels. Fluorescence detection was performed with the confocal laser scanning fluorescence imaging system described below. The fluorescence was excited with 46 mW of 488 nm light from a SpectraPhysics 2020 argon ion laser. A long pass dichroic beam splitter (Zeiss FT580) was used to reflect the laser beam down through a 100×, N.A. 1.3, oil immersion objective (Rolyn Optics) and onto the sample. The fluorescence emission was collected by the objective and passed through the beam splitter to the photodetector. The fluorescence emission passed though a spatial filter (200 mm pinhole, Melles Griot) to effect confocal detection and a long pass color filter (Schott RG610) before reaching a photomultiplier tube (RCA 31034 A). A computer controlled DC servo motor-driven XY translation stage (Design Components, Inc.) with a 6"×6" travel and 2.5 microcometer resolution was used to translate the gel past the laser beam at 3 cm/sec. A microcomputer (IBM PS/2 70-A21) with a Metra-Byte analog-to-digital board and a 8514/A graphic adapter was used to control the XY translation stage and to acquire and display images. The fluorescence images are pseudo-color encoded to represent different intensity levels and contrast stretched with a histogram equalization.method (Ekstrom, M. P. (1984) Digital Image Processing Techniques (Academic, NY)) to enhance the images. To quantitate the image data, the image columns that enclose the DNA bands were extracted and integrated.

RESULTS

In preparing the ethidium dimer dye non-covalently bound and intercalated DNA, formation of a red precipitate was noted at high concentrations of DNA (150 ng/μl) and ethidium dimer (EthD) 100 ng/μl. Down to a DNA concentration of 4 ng/μg and dye concentration of 1 ng/μl (or higher) some aggregate was still detectable after electrophoresis as an intensely fluorescent material in the portion of the gel immediately proximal to the well. Such material was not seen at lower DNA concentrations. Therefore, the data reported was at DNA concentrations of 1.5 ng/μl or lower. The observed fluorescence intensity of the DNA-EthD bands was at a maximum when the molar ratio of homodimer to DNA base pairs in the sample reached 1:4–5. Addition of further dye did not influence the band intensity significantly. Likewise, addition of DNA in excess of the 1:4 molar ratio of dye/base pairs had little effect on the fluorescence intensity. A standard ratio of dye to DNA of 1:4 by weight (approximately one dye molecule per five base pairs) was adopted.

Electrophoretic patterns given by nanogram amounts of DNA-EthD mixtures with dye/DNA weight ratios of 1:4 were equivalent to those given by microgram amounts of DNA visualized in parallel experiments by conventional staining with ethidium bromide. For the 1 kbp ladder DNA complex with EthD, the amount of DNA per band is about 60 pg.

The dependence of the fluorescence intensity of λDNA/Hind III restriction fragment bands on the amount of DNA applied to the gel and on the size of the fragments was determined. The obtained data showed that by comparison with appropriate standards, the sizes and amounts of DNA fragments in mixtures of unknown composition can be determined with a total amount of material ranging from 100 pg to 1 ng depending on the complexity of the mixture and the size range of the fragments. In one run, the detection of about 80 pg (quantitated by comparison with standards) of a 1.6 kbp fragment in a PCR amplification mixture was observed.

No indication of dissociation of the non-covalent DNA-EthD complexes was observed in the electrophoresis. To see whether the dye would redistribute in the presence of unlabeled DNA, a 50-fold molar excess of pUC18 DNA was added to preformed λDNA/Hind III-EthD complex and the mixture allowed to stand for varying periods of time before analysis by agarose gel electrophoresis. One-third of the dye remained with the λDNA/Hind III fragments after an hour of incubation with competing DNA. No further loss of the dye to the competing DNA was seen even after six hours of incubation. If the competing DNA and λDNA/Hind III fragments were mixed at a 50:1 molar ratio prior to the addition of the EthD, the dye was virtually quantitatively bound by the pUC18 DNA.

In order to recover the DNA free of the dye, it was found that quantitative removal of bound dye is achieved by using "Glassmilk" adsorbent as described above. The DNA eluted from the adsorbent was indistinguishable from the starting material in its band pattern on agarose gel electrophoresis and in its capacity to bind newly added EthD.

The subject methodology provides for numerous advantages, both in electrophoresis and in fluorescent label diagnostics, as compared to previous procedures, where ethidium bromide is added to the running buffer or the gel is stained after electrophoresis, and where high background interference in fluorescence detection is obtained, coupled with modest sensitivity because of the low affinity of ethidium bromide for DNA and the need to dispose of substantial quantities of mutagenic dye. These problems are resolved by the subject procedures. When photographic film is used for fluorescence detection, the sensitivity is low and the non-linear response of the film complicates quantitation. By employing a laser-induced fluorescence detection method, improved sensitivity is achieved, especially when optimized excitation conditions are employed. At the extreme end, single molecule detection can be demonstrated. High quality display and computer analysis is also readily achieved. The combination of micrometer spatial resolution and low detection limits provides for opportunities of enhanced sensitivity by using thinner gels and smaller sample spots to approach the detection limits of autoradiography with no sacrifice in electrophoretic resolution. The described procedures can be readily modified for the detection and quantitation of restriction fragments or other DNAs in high performance capillary zone electrophoresis. The subject complexes may also replace radiolabeled DNA in gel retardation experiments designed to detect high-affinity DNA binding proteins.

In the subject complexes, the DNA functions as a very specific rigid scaffold for holding many dye fluorophores at a specific distance and orientation such that radiationless processes competing with fluorescence emission are greatly reduced. Thus, the stable non-covalent complexes of the dimer with DNA can be used in a wide spectrum of applications as a new class of highly fluorescent probes carrying hundreds of dye molecules. The subject complexes can be joined to specific binding pair members to be used in the numerous procedures which employ complexation between specific binding pair-members, such as biotin and avidin. The subject complexes tailed with single-stranded DNA sequences can be used as specific hybridization probes for the detection of DNA sequences complementary to that of the tails. By using a variety of dyes in the DNA matrix, new fluorescent probes may be produced with unique properties.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

This invention was made with government support under DOE contract DE-FG03-88ER60706 awarded by the Department of Energy. The government has certain rights in the invention. The Applicants gratefully acknowledge sponsorship of this invention by National Science Foundation, Grant No. DMB 88-16727/DIR 87-20382.

What is claimed is:

1. In a method for performing a separation of a composition comprising employing an electrical field for directing movement of components in said composition in a differential manner, the improvement which comprises:

having present during said separation in said electrical field a moiety comprising (a) a probe having a double stranded DNA of at least about 20 base pairs and (b) non-covalently bound intercalated in said double stranded DNA at least one fluorescent molecule characterized by having at least two positive charges, having at least one fluorescent monomeric unit and having a binding affinity to double stranded DNA of at least about $5 \times 10^6$ $M^{-1}$ and up to about 1 fluorescent unit per 4 nucleotides in a nucleic acid strand, wherein said fluorescent unit is characterized by having at least one aromatic ring per monomeric unit.

2. A method according to claim 1, wherein said fluorescent molecule is a dimer and said monomeric units are phenanthridinium and/or acridinium.

3. A method according to claim 1, wherein said separation is gel electrophoresis and said method further comprises combining a probe having a double stranded DNA containing sample with said dimer prior to said separation.

4. A method according to claim 3, wherein said dimer has a plurality of positive charges.

5. A method according to claim 4, wherein said dimer is an ethidium dimer.

6. A method according to claim 2, wherein said moiety is joined to other than double stranded DNA.

7. A method according to claim 6, wherein said moiety comprises a polypeptide or saccharide.

8. The method according to claim 1, wherein said separating is by gel electrophoresis.

9. The method according to claim 8, wherein the individual bands "generated by gel electrophoresis" are detected.

10. The method according to claim 11, wherein said probe further comprises single stranded nucleic acid.

* * * * *